United States Patent
Suzuki et al.

(10) Patent No.: US 11,186,531 B2
(45) Date of Patent: Nov. 30, 2021

(54) PRODUCTION METHOD FOR ALKENE

(71) Applicant: Kureha Corporation, Tokyo (JP)

(72) Inventors: Kensuke Suzuki, Tokyo (JP); Hiraku Tohmiya, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 16/978,861

(22) PCT Filed: Oct. 18, 2018

(86) PCT No.: PCT/JP2018/038759
§ 371 (c)(1),
(2) Date: Sep. 8, 2020

(87) PCT Pub. No.: WO2019/176151
PCT Pub. Date: Sep. 19, 2019

(65) Prior Publication Data
US 2021/0047252 A1    Feb. 18, 2021

(30) Foreign Application Priority Data
Mar. 14, 2018    (JP) .............................. JP2018-046759

(51) Int. Cl.
*C07C 17/25* (2006.01)
*B01J 31/02* (2006.01)
*C07C 21/18* (2006.01)

(52) U.S. Cl.
CPC ........... *C07C 17/25* (2013.01); *B01J 31/0239* (2013.01); *B01J 2531/98* (2013.01); *C07C 21/18* (2013.01)

(58) Field of Classification Search
CPC ...... C07C 17/25; C07C 21/18; B01J 31/0239; B01J 2531/98
See application file for complete search history.

(56) References Cited

U.S. PATENT DOCUMENTS

| | | | |
|---|---|---|---|
| 7,345,209 B2 | 3/2008 | Mukhopadhyay et al. | |
| 7,714,177 B2 | 5/2010 | Mukhopadhyay et al. | |
| 8,338,652 B2 | 12/2012 | Terada et al. | |
| 8,927,791 B2 | 1/2015 | Bektesevic et al. | |
| 9,040,759 B2 | 5/2015 | Wang et al. | |
| 9,963,410 B2 | 5/2018 | Karube et al. | |
| 2005/0090698 A1 | 4/2005 | Merkel et al. | |
| 2005/0245773 A1 | 11/2005 | Mukhopadhyay et al. | |
| 2008/0103341 A1 | 5/2008 | Mukhopadhyay et al. | |
| 2009/0043136 A1 | 2/2009 | Wang et al. | |
| 2010/0204529 A1* | 8/2010 | Terada .................. C07C 17/23 570/160 |
| 2011/0270000 A1 | 11/2011 | Bektesevic et al. | |
| 2012/0302803 A1 | 11/2012 | Yamashita et al. | |
| 2015/0368169 A1 | 12/2015 | Wang et al. | |
| 2018/0044268 A1 | 2/2018 | Karube et al. | |
| 2018/0162794 A1 | 6/2018 | Ichinokawa et al. | |

FOREIGN PATENT DOCUMENTS

| | | |
|---|---|---|
| CN | 105384596 A | 3/2016 |
| JP | H11-100335 A | 4/1999 |
| JP | 2007-535570 A | 12/2007 |
| JP | 2010-529111 A | 8/2010 |
| JP | 2010-215659 A | 9/2010 |
| JP | 2010-532762 A | 10/2010 |
| JP | 2013-519631 A | 5/2013 |
| JP | 2013-528585 A | 7/2013 |
| JP | 2016-164152 A | 9/2016 |
| WO | 2017/018412 A1 | 2/2017 |

OTHER PUBLICATIONS

International Search Report of the International Searching Authority for PCT/JP2018/038759 dated Jan. 8, 2019.
English translation of International Search Report of the International Searching Authority for PCT/JP2018/038759 dated Jan. 8, 2019.
Written Opinion of the International Searching Authority dated Jan. 8, 2019, in PCT/JP2018/038759.
Japanese Notification of Reasons for Refusal for Japanese Application No. 2018-046759, dated Aug. 3, 2021, with an English translation.

* cited by examiner

*Primary Examiner* — Jafar F Parsa
(74) *Attorney, Agent, or Firm* — Birch, Stewart, Kolasch & Birch, LLP

(57) ABSTRACT

The present invention is to provide a method of producing an alkene that can further enhance the yield of an alkene, a reaction product, the method including bringing a gaseous halogenated alkane into contact with an alkaline aqueous solution in the presence of a phase-transfer catalyst. The objective above is achieved by a method of producing an alkene comprising bringing in the presence of a phase-transfer catalyst a liquid phase containing an alkaline aqueous solution and a water-insoluble solvent into contact with a gas phase containing a halogenated alkane that is soluble in the water-insoluble solvent.

6 Claims, No Drawings

PRODUCTION METHOD FOR ALKENE

TECHNICAL FIELD

The present invention relates to a method of producing an alkene.

BACKGROUND ART

As a method of producing an alkene, a method for an elimination reaction of a hydrogen halide from a halogenated alkane that is substituted with a plurality of halogen atoms has been known. For example, Patent Document 1 and Patent Document 2 describe a method, in which a gaseous halogenated alkane is brought into contact with a catalyst at a high temperature of 200° C. or higher and a high pressure to cause an elimination reaction of the hydrogen halide to occur.

In contrast, in recent years, methods where a gaseous halogenated alkane is brought into contact with an alkaline aqueous solution in the presence of a phase-transfer catalyst to cause an elimination reaction of the hydrogen halide to occur have been reported. For example, according to a method in Patent Document 3, an elimination reaction of hydrogen halide can be performed in a lower temperature region, namely from 60° C. to 200° C., and in a lower pressure region, namely from 0.8 to 5.0 MPa. Furthermore, according to a method in Patent Document 4, a dehydrohalogenation can be performed in a temperature range that is higher than 40° C. but 80° C. or lower.

CITATION LIST

Patent Document

Patent Document 1: JP 2007-535570 T
Patent Document 2: JP 2010-532762 T
Patent Document 3: CN 105384596 A
Patent Document 4: JP 2013-528585 T

SUMMARY OF INVENTION

Technical Problem

In these methods described in Patent Document 3 and Patent Document 4, it is expected that an alkene can be produced at lower costs using less energy because the elimination of a hydrogen halide from a halogenated alkane can be performed at a lower temperature with a lower pressure.

However, when the present inventors investigated, even with the methods described in Patent Document 3 and Patent Document 4, the yield of the alkene, the reaction product, was not enhanced as much as expected.

The present invention was completed in light of the problems described above, and an object of the present invention is to provide a method of producing an alkene that can further enhance the yield of the alkene which is a reaction product, the method including bringing a gaseous halogenated alkane into contact with an alkaline aqueous solution in the presence of a phase-transfer catalyst.

Solution to Problem

The method of producing an alkene according to an embodiment of the present invention to achieve the above object includes bringing a liquid phase containing an alkaline aqueous solution and a water-insoluble solvent into contact with a gas phase containing a halogenated alkane that is soluble in the water-insoluble solvent, in the presence of a phase-transfer catalyst.

Advantageous Effects of Invention

According to the present invention, provided is a method of producing an alkene that can further enhance the yield of the alkene which is a reaction product, the method including bringing a gaseous halogenated alkane into contact with an alkaline aqueous solution in the presence of a phase-transfer catalyst.

DESCRIPTION OF EMBODIMENTS

As a result of diligent study of the object described above, the present inventors found that the yield of the alkene, which is a reaction product, can be further enhanced by bringing in the presence of a phase-transfer catalyst a liquid phase containing an alkaline aqueous solution and a water-insoluble solvent into contact with a gas phase containing a halogenated alkane that is soluble in the water-insoluble solvent so as to cause an elimination reaction of a hydrogen halide to occur more efficiently. Further research and experiment were thus performed, and the present invention was completed.

According to the method, the liquid phase is in a condition where the alkaline aqueous solution and the water-insoluble solvent are separated, or either of the alkaline liquid or the water-insoluble solvent is dispersed in the other liquid. When the gas phase is brought into contact with such a liquid phase, the halogenated alkane is dissolved in the water-insoluble solvent, and thus reaction efficiency is further enhanced. It is thus conceived that the yield of the alkene, which is the reaction product, is further enhanced.

The liquid phase contains the alkaline aqueous solution and the water-insoluble solvent, and further contains the phase-transfer catalyst.

The alkaline aqueous solution can be, for example, an aqueous solution formed by dissolving an oxide of alkali metal atom or alkaline earth metal atom or an alkaline compound such as hydroxide in water, which is a solvent. Examples of the alkaline compound include potassium hydroxide (KOH), sodium hydroxide (NaOH), lithium hydroxide (LiOH), magnesium hydroxide ($Mg(OH)_2$), calcium hydroxide ($Ca(OH)_2$), and calcium oxide (CaO). Among these, potassium hydroxide (KOH) and sodium hydroxide (NaOH) are preferred, and sodium hydroxide (NaOH) is more preferred.

A greater content of the alkaline compound in the alkaline aqueous solution tends to further increase the reaction efficiency. From the perspective of further enhancing the reaction efficiency while preventing the deterioration of reaction vessels and pipes, the content of the alkaline compound in the alkaline aqueous solution is preferably from 1 mass % to 70 mass %, more preferably from 10 mass % to 60 mass %, and even more preferably from 30 mass % to 50 mass %, relative to the total mass of the alkaline aqueous solution. Needless to say, the content of the alkaline compound can be appropriately decided depending on the type of the halogenated alkane that causes the elimination reaction of hydrogen halide.

The phase-transfer catalyst causes an elimination reaction of hydrogen halide to occur by the action between the alkaline compound contained in the alkaline aqueous solution and the halogenated alkane that is sparingly insoluble in the alkaline aqueous solution so as to allow an anion derived from the alkaline compound (e.g. OH⁻ ion) to act as a base.

Furthermore, in the present invention, it is conceived that the phase-transfer catalyst promotes the transfer of the anion acting as a base to the water-insoluble solvent. Therefore, in the present invention, because both of the halogenated alkane dissolved from the gas phase and the anion acting as a base, which is promoted to be transferred by the phase-transfer catalyst can be present in high concentration in the water-insoluble solvent, it is conceived that the elimination reaction of the hydrogen halide from the halogenated alkane is further efficiently proceeded.

The phase-transfer catalyst may be a known phase-transfer catalyst, and examples include crown ethers, onium salts, cryptates, polyalkylene glycols, and derivatives of these.

Examples of the crown ether include 18-crown-6, 15-crown-5, and 12-crown-4. Examples of the derivative of the crown ether include dibenzo-18-crown-6, dicyclohexano-18-crown-6, and dibenzo-24-crown-8.

Examples of the onium salt include quaternary phosphonium salts and quaternary ammonium salts. Examples of the quaternary phosphonium salt include tetra-n-butylphosphonium chloride, tetraphenylphosphonium bromide, tetraphenylphosphonium chloride, triphenylmethylphosphonium bromide, triphenylmethylphosphonium chloride, bis[tris(dimethylamino)phosphine]iminium chloride, and tetratris[tris(dimethylamino)phosphineimino]phosphonium chloride. Examples of the quaternary ammonium salt include tetramethylammonium chloride, tetramethylammonium bromide, benzyltriethylammonium chloride, methyl trioctylammonium chloride, tetrabutylammonium chloride, tetrabutylammonium bromide, tetradecyltrimethylammonium bromide, tetradecyltrimethylammonium chloride, hexadecyltrimethylammonium bromide, hexadecyltrimethylammonium chloride, and tetrabutylammonium hydrogen sulfate. Examples of other onium salts include 4-dialkylaminopyridinium salt and tetraphenylarsonium chloride.

Examples of the polyalkylene glycol compound include glycols and alkyl ether compounds of the glycols. Examples of the glycols include diethylene glycol, triethylene glycol, tetraethylene glycol, pentaethylene glycol, hexaethylene glycol, diisopropylene glycol, dipropylene glycol, tripropylene glycol, tetrapropylene glycol, and tetramethylene glycol. Examples of the alkyl ether compounds of the glycols include monoalkyl ethers of these glycols (e.g., monomethyl ether compounds, monoethyl ether compounds, monopropyl ether compounds, and monobutyl ether compounds), dialkyl ethers (specifically, tetraethylene glycol dimethyl ether and pentaethylene glycol dimethyl ether), phenyl ethers, benzyl ethers, and polyalkylene glycols (specifically, polyethylene glycol (average molecular weight: approximately 300) dimethyl ether, polyethylene glycol (average molecular weight: approximately 300) dibutyl ether, and polyethylene glycol (average molecular weight: approximately 400) dimethyl ether).

The cryptate is a three-dimensional polymacrocyclic chelating agent formed by linking a bridgehead structure with a chain containing appropriately separated donor atoms. Examples of the cryptate include bicyclic molecules obtained by linking a nitrogen bridgehead with an (—OCH₂CH₂—) chain, such as 2.2.2-cryptate-4,7,13,16,21,24-hexaoxa-1,10-diazabicyclo[8.8.8]hexacosane.

The content of the phase-transfer catalyst in the reaction system is preferably from 0.01 mass % to 3 mass %, more preferably from 0.05 mass % to 1 mass %, and even more preferably from 0.1 mass % to 0.5 mass %, relative to the total mass of the alkaline compound in the alkaline aqueous solution.

The water-insoluble solvent is not compatible with the alkaline aqueous solution and has only to be an organic solvent that forms a phase that is different from the alkaline aqueous solution in the liquid phase and that can adequately dissolve the halogenated alkane. Note that the water-insoluble solvent means an organic solvent having a solubility in water of 10% or less. Examples of the water-insoluble solvent include alcohol-based water-insoluble solvents, ether-based water-insoluble solvents, aliphatic hydrocarbon-based water-insoluble solvents, and aromatic hydrocarbon-based water-insoluble solvents. Among these, ether-based water-insoluble solvents, aliphatic hydrocarbon-based water-insoluble solvents, and aromatic hydrocarbon-based water-insoluble solvents are preferred, and aromatic hydrocarbon-based water-insoluble solvents are more preferred.

Examples of the alcohol-based water-insoluble solvents include octanol.

Examples of the ether-based water-insoluble solvents include diethyl ether, dipropyl ether, methylpropyl ether, methylisopropyl ether, methylbutyl ether, methylisobutyl ether, methyl-sec-butyl ether, methyl-tert-butyl ether, methylpentyl ether, methylisopentyl ether, methylneopentyl ether, methylhexyl ether, methylheptyl ether, methyloctyl ether, methylnonyl ether, ethylpropyl ether, ethylisopropyl ether, ethylbutyl ether, ethylisobutyl ether, ethyl-sec-butyl ether, ethyl-tert-butyl ether, ethylpentyl ether, ethylisopentyl ether, ethylneopentyl ether, ethylhexyl ether, ethylheptyl ether, ethyloctyl ether, propylisopropyl ether, diisopropyl ether, propylbutyl ether, propylisobutyl ether, propyl-sec-butyl ether, propyl-tert-butyl ether, propylpentyl ether, propylisopentyl ether, propylneopentyl ether, propylhexyl ether, propylheptyl ether, butylisobutyl ether, butyl-sec-butyl ether, butyl-tert-butyl ether, diisobutyl ether, di-sec-butyl ether, di-tert-butyl ether, butylpentyl ether, isobutylpentyl ether, sec-butylpentyl ether, tert-butylpentyl ether, butylisopentyl ether, isobutylisopentyl ether, sec-butylisopentyl ether, tert-butylisopentyl ether, butylneopentyl ether, isobutylneopentyl ether, sec-butylneopentyl ether, tert-butylneopentyl ether, dipentyl ether, pentylisopentyl ether, pentylneopentyl ether, diisopentyl ether, isopentylneopentyl ether, dineopentyl ether, and cyclopentylmethyl ether.

Examples of the aliphatic hydrocarbon-based water-insoluble solvents include pentane, hexane, heptane, octane, nonane, decane, dodecane, undecane, tridecane, decalin, 2,2,4,6,6-pentamethylheptane, cyclohexane, methylcyclohexane, 1,2-dimethylcyclohexane, 1,3-dimethylcyclohexane, 1,4-dimethylcyclohexane, ethylcyclohexane, 1,2,4-trimethylcyclohexane, 1,3,5-trimethylcyclohexane, propylcyclohexane, butylcyclohexane, and paraffins.

Examples of the aromatic hydrocarbon-based water-insoluble solvents include benzene, toluene, o-xylene, m-xylene, p-xylene, ethylbenzene, trimethylbenzene, ethyltoluene, propylbenzene, isopropylbenzene, 1,2,3-trimethylbenzene, 1,2,4-trimethylbenzene, 1,3,5-trimethylbenzene, 2-ethyltoluene, 3-ethyltoluene, 4-ethyltoluene, cymene, chlorobenzene, o-dichlorobenzene, m-dichlorobenzene, p-dichlorobenzene, tetralin, and anisole.

Note that the water-insoluble solvents may be a vegetable oil, such as soybean oil, sesame oil, olive oil, and cottonseed oil.

Among these water-insoluble solvents, paraffins, toluene, isopropylbenzene, and o-dichlorobenzene are preferred, toluene, isopropylbenzene, and o-dichlorobenzene are more preferred, and o-dichlorobenzene is even more preferred.

The content of the water-insoluble solvent in the reaction system is preferably from 0.01 times to 10 times, more preferably from 0.1 times to 5 times, and even more preferably from 0.5 times to 2 times the total mass of the halogenated alkane.

From the perspective of facilitating contact with the gas phase, the water-insoluble solvent is preferably a solvent having a specific gravity that is less than that of the alkaline aqueous solution. However, when the liquid phase is agitated, the water-insoluble solvent may be a solvent having a greater specific gravity than that of the alkaline aqueous solution.

The gas phase contains the halogenated alkane, and further contains alkene, which is the reaction product, after the reaction proceeded.

The halogenated alkane is a molecule having at least one halogen atom and at least one hydrogen atom in one molecule and is a gas at normal temperature. The halogenated alkane forms an alkene by contact with the liquid phase in the presence of the phase-transfer catalyst and by elimination of the halogen atom with the hydrogen bonded to a carbon atom adjacent to the halogen atom as a hydrogen halide.

Note that the halogenated alkane may be a molecule having at least two halogen atoms and at least one hydrogen atom in one molecule and may be a gas at normal temperature. Such a halogenated alkane forms a halogenated alkene by contact with the liquid phase in the presence of the phase-transfer catalyst and by elimination of one of the at least two halogen atoms (one having a smaller bond dissociation energy with a carbon atom) with the hydrogen bonded to the adjacent carbon atom as a hydrogen halide.

Examples of the halogen atom include a fluorine (F) atom, a chlorine (Cl) atom, a bromine (Br) atom, and an iodine (I) atom.

Examples of the halogenated alkane include fluoroethane, 1,1-difluoroethane, 1,1,1-trifluoroethane, 1,1,1,2-tetrafluoroethane, 1,1,2,2-tetrafluoroethane, 1,1,1,2,2-pentafluoroethane, chloroethane, 1,1-dichloroethane, 1,2-dichloroethane, 1,1,2-trichloroethane, 1,1-difluoro-1-chloroethane, 1,2-dichloropropane, 1,3-dichloropropane, 1,2,3-trichloropropane, 1,1,1,2,2-pentafluoropropane, 1,1,1,3,3-pentafluoropropane, 1,1,1,2,3,3-hexafluoropropane, 1,1,1,3,3,3-hexafluoropropane, 1,1,1,2,3,3,3-heptafluoropropane, 1,1,1,2-tetrafluoro-2-chloropropane, 1,1,1,2-tetrafluoro-3-chloropropane, 1,1,1,2,2-pentafluoro-3,3-dichloropropane, 1,1,1-trifluoro-2,2-dichloropentane, 1,1,1,2-tetrafluoro-2-chloropentane, 1,1,1,2,3-pentafluoropentane, 1,1,1,2-tetrafluoro-3-chloropentane, 1,1,1,3-tetrafluoro-3-chloropentane, 1,2-dichlorobutane, and 1,4-dichlorobutane.

Among these, 1,1-difluoro-1-chloroethane, 1,1,1,2-tetrafluoro-2-chloropropane, 1,1,1,2-tetrafluoro-3-chloropropane, 1,1,1,2,2-pentafluoropropane, and 1,1,1,2,2-pentafluoro-3,3-dichloropropane are preferred.

The halogenated alkane is preferably a halogenated alkane represented by General Formula (1).

[Chem. 1]

GENERAL FORMULA (1)

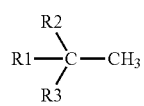

In General Formula (1), R1 represents a halogen atom, R2 represents a hydrogen atom, a halogen atom that is the same type as R1, or a halogen atom having a bond dissociation energy with a carbon atom greater than that of the atom represented by R1, R3 represents a halogen atom that is the same type as R1, a halogen atom having a bond dissociation energy with a carbon atom greater than that of the atom represented by R1, or an alkyl group having from 1 to 3 carbons which may be substituted with any halogen atom.

From the halogenated alkane represented by General Formula (1), by elimination of the hydrogen halide (R1-H), a halogenated alkene represented by General Formula (2) is formed.

[Chem. 2]

GENERAL FORMULA (2)

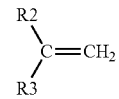

In General Formula (2), R2 is the same as R2 in General Formula (1) and represents a hydrogen atom or a halogen atom, R3 is the same as R3 in General Formula (1) and represents a halogen atom or an alkyl group having from 1 to 3 carbons which may be substituted with any halogen atom.

Note that, in General Formula (1) and General Formula (2), the halogen atom represented by R1, the halogen atoms represented by R2 and R3, and the halogen atom substituting the alkyl group represented by R3 may be the same type or different type of atoms.

Furthermore, in General Formula (2), when R3 is an alkyl group substituted with a halogen atom, the alkyl group may be substituted by a plurality of halogen atoms, or all the hydrogens may be substituted by halogen atoms. At this time, the plurality of halogen atoms used for the substitution may be all the same type of atoms or may be a combination of different types of plurality of halogen atoms.

In General Formula (1) and General Formula (2), R1 is preferably a fluorine (F) atom, a chlorine (Cl) atom, or a bromine (Br) atom, and more preferably a chlorine (Cl) atom or a bromine (Br) atom, and even more preferably a chlorine (Cl) atom.

Furthermore, from the perspective of facilitating elimination of the hydrogen halide, in General Formula (1) and General Formula (2), preferably R2 or R3 is a fluorine (F) atom, and more preferably both R2 and R3 are fluorine (F) atoms.

For example, the halogenated alkane can be 1,1-difluoro-1-chloroethane, and the halogenated alkene, which is the reaction product at this time, can be 1,1-difluoroethylene (vinylidene fluoride).

The content of the halogenated alkane in the reaction system is preferably from 0.03 mass % to 6 mass %, more preferably from 0.3 mass % to 5 mass %, and even more preferably from 1 mass % to 4 mass %, relative to the total mass of the reaction solution containing the phase-transfer catalyst in the reaction system.

Note that the gas phase may contain an inert gas, such as a nitrogen ($N_2$) gas and an argon (Ar) gas; however, from the perspective of further enhancing the reaction efficiency, the gas phase preferably substantially only contains the halogenated alkane and the reaction product. "Substantially"

means 99 vol % or greater of the gas phase is the halogenated alkane and the reaction product.

The method of producing an alkene described above has only to include a step of bringing the liquid phase and the gas phase into contact with each other. At this time, agitation of the liquid phase is preferred from the perspective of further enhancing the yield of the alkene, which is the reaction product, by enlarging a contact area between the water-insoluble solvent that is finely dispersed in the alkaline aqueous solution and the alkaline aqueous solution containing a greater amount of base causing the elimination reaction of the hydrogen halide.

Thereafter, the method of producing an alkene described above may further include a step of recovering the alkene, which is the reaction product, by separating the alkene from the gas phase after the contact. The separation and recovery can be performed by known methods.

The method of producing an alkene described above can be performed, for example, by forming the liquid phase by charging the alkaline aqueous solution, the phase-transfer catalyst, and the water-insoluble solvent in a reaction vessel having an adequate capacity and then introducing the halogenated alkane in a gas form into the reaction vessel.

The liquid phase may be prepared in a reaction vessel by charging the alkaline aqueous solution, the phase-transfer catalyst, and the water-insoluble solvent in the reaction vessel. Alternatively, the liquid phase that was prepared by mixing these in advance may be charged in the reaction vessel described above. The order of these charging and mixing is not particularly limited.

Furthermore, it is preferable to discharge the gas component inside of the vessel by reducing the pressure inside of the reaction vessel before the introduction of the halogenated alkane. After the pressure reduction, before the introduction of the halogenated alkane, an inert gas may be introduced into the reaction vessel.

After the introduction of the halogenated alkane, inside of the reaction vessel may be heated to promote the elimination reaction of the halogenated alkane. The temperature inside of the reaction vessel at this time (reaction temperature) can be 20° C. or higher and lower than 200° C., and is preferably from 20° C. to 140° C., more preferably from 40° C. to 100° C., and even more preferably from 40° C. to 80° C.

Furthermore, the pressure inside of the reaction vessel after the introduction of the halogenated alkane can be not less than atmospheric pressure and 5.0 MPa or less, and is preferably not less than atmospheric pressure and 2.0 MPa or less, more preferably not less than atmospheric pressure and 0.8 MPa or less, even more preferably from 0.1 MPa to 0.5 MPa, and particularly preferably 0.1 MPa to 0.3 MPa.

Furthermore, the reaction time after the introduction of the halogenated alkane has only to be approximately from 0.5 hours to 8 hours.

EXAMPLES

Hereinafter, specific examples of the present invention will be described together with comparative examples, but the present invention is not limited thereto.

Example 1

In a 1 L pressure-resistant reaction vessel with an agitator (hereinafter, also simply referred to as "reaction vessel"), 409.7 g of 50 mass % NaOH aqueous solution was added. And then, all of the amount of an aqueous solution obtained by completely dissolving 0.5013 g of tetrabutylammonium bromide in 106.5 g of water was charged in the reaction vessel. Thereafter, 5.7 g of liquid paraffin was charged in the reaction vessel, the reaction vessel was completely tightclosed and the pressure inside of the reaction vessel was reduced by a vacuum pump, and 9.2 g of 1,1-difluoro-1-chloroethane (R-142b) was charged. After the charging was completed, agitation was started, and the temperature was increased to 80° C. After it was confirmed that the internal temperature reached 80° C., the temperature was maintained for 3 hours. The pressure in the reaction vessel while the temperature was maintained was from 0.22 MPa to 0.23 MPa. After 3 hours, the heating was terminated. The reaction solution was cooled to 40° C. or lower, and then the gas phase sample was collected in a gas collection bag. The collected gas phase sample was analyzed by gas chromatography (GC-2014, available from Shimadzu Corporation; column: CP-PoraPLOT Q ("PoraPLOT" is a registered trademark of Agilent Technologies, Inc.) available from Agilent Technologies, Inc.). The analysis temperature was maintained at 40° C. for 10 minutes, then increased to 200° C. at a temperature increasing rate of 10° C./min, and then maintained at 200° C. for 25 minutes. The analysis result showed 43.7 GC area % of 1,1-difluoroethylene (VDF) and 56.2 GC area % of 1,1-difluoro-1-chloroethane (R-142b).

Example 2

In a reaction vessel, 409.7 g of 50 mass % NaOH aqueous solution was added. And then, all of the amount of an aqueous solution obtained by completely dissolving 0.5011 g of tetrabutylammonium bromide in 96.5 g of water was charged in the reaction vessel. Thereafter, 10.0 g of toluene was charged in the reaction vessel, the reaction vessel was completely tightly closed and the pressure inside of the reaction vessel was reduced by a vacuum pump, and 14.9 g of 1,1-difluoro-1-chloroethane (R-142b) was charged. After the charging was completed, agitation was started, and the temperature was increased to 80° C. After it was confirmed that the internal temperature reached 80° C., the temperature was maintained for 3 hours. The pressure in the reaction vessel while the temperature was maintained was from 0.28 MPa to 0.40 MPa. After 3 hours, the heating was terminated. The reaction solution was cooled to 40° C. or lower, and then the gas phase sample was collected in a gas collection bag. The collected gas phase sample was analyzed by gas chromatography in the same manner as in Example 1. The analysis result showed 74.1 GC area % of 1,1-difluoroethylene (VDF) and 20.5 GC area % of 1,1-difluoro-1-chloroethane (R-142b).

Example 3

In a reaction vessel, 410.5 g of 50 mass % NaOH aqueous solution was added. And then, all of the amount of an aqueous solution obtained by completely dissolving 0.5013 g of tetrabutylammonium bromide in 95.7 g of water was charged in the reaction vessel. Thereafter, 8.6 g of isopropylbenzene was charged in the reaction vessel, the reaction vessel was completely tightly closed and the pressure inside of the reaction vessel was reduced by a vacuum pump, and 11.9 g of 1,1-difluoro-1-chloroethane (R-142b) was charged. After the charging was completed, agitation was started, and the temperature was increased to 80° C. After it was confirmed that the internal temperature reached 80° C., the temperature was maintained for 3 hours. The pressure in the reaction vessel while the temperature was maintained was from 0.40 MPa to 0.47 MPa. After 3 hours, the heating was terminated. The reaction solution was cooled to 40° C. or lower, and then the gas phase sample was collected in a gas collection bag. The collected gas phase sample was analyzed by gas chromatography in the same manner as in Example 1. The analysis result showed 75.8 GC area % of 1,1-difluoroethylene (VDF) and 22.5 GC area % of 1,1-difluoro-1-chloroethane (R-142b).

Example 4

In a reaction vessel, 410.5 g of 50 mass % NaOH aqueous solution was added. And then, all of the amount of an aqueous solution obtained by completely dissolving 0.5016 g of tetrabutylammonium bromide in 95.7 g of water was charged in the reaction vessel. Thereafter, 13.0 g of o-dichlorobenzene was charged in the reaction vessel, the reaction vessel was completely tightly closed and the pressure inside of the reaction vessel was reduced by a vacuum pump, and 8.7 g of 1,1-difluoro-1-chloroethane (R-142b) was charged. After the charging was completed, agitation was started, and the temperature was increased to 80° C. After it was confirmed that the internal temperature reached 80° C., the temperature was maintained for 3 hours. The pressure in the reaction vessel while the temperature was maintained was from 0.27 MPa to 0.31 MPa. After 3 hours, the heating was terminated. The reaction solution was cooled to 40° C. or lower, and then the gas phase sample was collected in a gas collection bag. The collected gas phase sample was analyzed by gas chromatography in the same manner as in Example 1. The analysis result showed 88.5 GC area % of 1,1-difluoroethylene (VDF) and 11.1 GC area % of 1,1-difluoro-1-chloroethane (R-142b).

Example 5

In a reaction vessel, 410.5 g of 50 mass % NaOH aqueous solution was added. And then, all of the amount of an aqueous solution obtained by completely dissolving 0.5013 g of tetrabutylammonium bromide in 95.7 g of water was charged in the reaction vessel. Thereafter, 13.0 g of o-dichlorobenzene was charged in the reaction vessel, the reaction vessel was completely tightly closed and the pressure inside of the reaction vessel was reduced by a vacuum pump, and 8.7 g of 1,1-difluoro-1-chloroethane (R-142b) was charged. After the charging was completed, agitation was started, and the temperature was increased to 80° C. After it was confirmed that the internal temperature reached 80° C., the temperature was maintained for 6 hours. The pressure in the reaction vessel while the temperature was maintained was from 0.21 MPa to 0.24 MPa. After 6 hours, the heating was terminated. The reaction solution was cooled to 40° C. or lower, and then the gas phase sample was collected in a gas collection bag. The collected gas phase sample was analyzed by gas chromatography in the same manner as in Example 1. The analysis result showed 93.1 GC area % of 1,1-difluoroethylene (VDF) and 6.1 GC area % of 1,1-difluoro-1-chloroethane (R-142b).

Comparative Example 1

In a reaction vessel, 409.7 g of 50 mass % NaOH aqueous solution was added. And then, all of the amount of an aqueous solution obtained by completely dissolving 0.5008 g of tetrabutylammonium bromide in 106.5 g of water was charged in the reaction vessel. Thereafter, the reaction vessel was completely tightly closed and the pressure inside of the vessel was reduced by a vacuum pump, and 10.4 g of 1,1-difluoro-1-chloroethane (R-142b) was charged. After the charging was completed, agitation was started, and the temperature was increased to 80° C. After it was confirmed that the internal temperature reached 80° C., the temperature was maintained for 3 hours. The pressure in the reaction vessel while the temperature was maintained was from 0.25 MPa to 0.26 MPa. After 3 hours, the heating was terminated. The reaction solution was cooled to 40° C. or lower, and then the gas phase sample was collected in a gas collection bag. The collected gas phase sample was analyzed by gas chromatography in the same manner as in Example 1. The analysis result showed 25.5 GC area % of 1,1-difluoroethylene (VDF) and 74.5 GC area % of 1,1-difluoro-1-chloroethane (R-142b).

As is clear from these results, when a liquid phase containing an alkaline aqueous solution and a water-insoluble solvent is brought into contact with a gas phase containing a halogenated alkane that is soluble in the water-insoluble solvent in the presence of a phase-transfer catalyst, the yield of an alkene was enhanced compared to the case where the liquid phase contained no water-insoluble solvent was used.

The present application claims priority to the Japanese Patent Application No. 2018-046759 filed on Mar. 14, 2018, and the contents of the claims and the specification of this application are incorporated into the present application.

INDUSTRIAL APPLICABILITY

According to the method of producing an alkene of the present invention, an alkene, such as halogenated alkene, can be more efficiently produced. Therefore, the present invention is expected to contribute to the development and dissemination of the technologies, for example, in the field of synthesis involving an alkene such as halogenated alkene.

The invention claimed is:
1. A method of producing an alkene, the method comprising bringing in the presence of a phase-transfer catalyst a liquid phase containing an alkaline aqueous solution and a water-insoluble solvent into contact with a gas phase containing a halogenated alkane that is soluble in the water-insoluble solvent and is represented by General Formula (1), and eliminating hydrogen chloride, wherein
a content of the halogenated alkane in a reaction system is from 1 mass % to 4 mass %, relative to a total mass of a reaction solution containing the phase-transfer catalyst in the reaction system:

[Chem. 1]

GENERAL FORMULA (1)

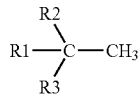

where, R1 represents a chlorine atom, R2 represents a hydrogen atom, a halogen atom that is the same type as R1, or a halogen atom having a bond dissociation energy with a carbon atom greater than that of the atom represented by R1, R3 represents a halogen atom that is the same type as R1, a halogen atom having a bond dissociation energy with a carbon atom greater than that of the atom represented by R1, or an alkane group having from 1 to 3 carbons which may be substituted with any halogen atom.

2. The method of producing an alkene according to claim 1, wherein the liquid phase is agitated in the step of bringing the liquid phase into contact with the gas phase.

3. The method of producing an alkene according to claim 1, wherein the step of bringing the liquid phase into contact with the gas phase is a step of producing the alkene in a gas form, which is a reaction product.

4. The method of producing an alkene according to claim 1, wherein the water-insoluble solvent is a water-insoluble solvent selected from a group consisting of an alcohol-based water-insoluble solvent, an ether-based water-insoluble solvent, an aliphatic hydrocarbon-based water-insoluble solvent, and an aromatic hydrocarbon-based water-insoluble solvent.

5. The method of producing an alkene according to claim 1, wherein the water-insoluble solvent is a water-insoluble solvent selected from a group consisting of toluene, isopropylbenzene, and o-dichlorobenzene.

6. The method of producing an alkene according to claim 1, wherein
the halogenated alkane is 1,1-difluoro-1-chloroethane, and
the step of bringing the liquid phase into contact with the gas phase is a step of producing 1,1-difluoroethylene.

* * * * *